United States Patent [19]
Jaffe et al.

[11] B 3,985,815
[45] Oct. 12, 1976

[54] AQUEOUS CRYSTALLIZATION OF XYLITOL

[75] Inventors: Gerald Myer Jaffe, Verona; Peter Hans Weinert, Wayne, both of N.J.

[73] Assignee: Hoffmann-La Roche Inc., Nutley, N.J.

[22] Filed: Oct. 31, 1974

[21] Appl. No.: 519,446

[44] Published under the second Trial Voluntary Protest Program on February 24, 1976 as document No. B 519,446.

Related U.S. Application Data

[63] Continuation of Ser. No. 296,404, Oct. 10, 1972, abandoned.

[52] U.S. Cl. .............................. 260/637 R; 127/37; 260/635 C; 426/658
[51] Int. Cl.$^2$.................. C07C 27/26; C07C 29/24
[58] Field of Search .................... 260/635 C, 637 R

[56] References Cited
UNITED STATES PATENTS

| | | | |
|---|---|---|---|
| 2,749,371 | 6/1956 | Kasehagen | 260/635 C |
| 2,752,270 | 6/1956 | Specht | 260/635 C |
| 2,917,390 | 12/1959 | Apel et al. | 260/635 C |
| 2,989,569 | 6/1961 | Apel et al. | 260/635 C |
| 3,558,725 | 1/1971 | Kohno et al. | 260/635 C |
| 3,586,537 | 6/1971 | Steiner et al. | 260/635 C |
| 3,627,636 | 12/1971 | Jaffe et al. | 260/635 C |
| 3,784,408 | 1/1974 | Jaffe et al. | 260/635 C |

OTHER PUBLICATIONS

Vogel, "Practical Organic Chemistry," 3rd ed. (1957), pp. 122 to 132.

*Primary Examiner*—Joseph E. Evans
*Attorney, Agent, or Firm*—Samuel L. Welt; Bernard S. Leon; Richard A. Gaither

[57] ABSTRACT

A process for obtaining crystalline xylitol substantially free of xylose from a mixture of xylose and xylitol by providing an aqueous solution of about 50 to 75 weight percent xylitol, no more than about 5 weight percent xylose and about 20 to 45 weight percent water and fractionally crystallizing xylitol from the aqueous solution to provide crystalline xylitol containing no more than about 0.10 weight percent xylose.

3 Claims, No Drawings

AQUEOUS CRYSTALLIZATION OF XYLITOL

This is a continuation of application Ser. No. 296,404 filed Oct. 10, 1972 entitled "AQUEOUS CRYSTALLIZATION OF XYLITOL" and now abandoned.

BACKGROUND OF THE INVENTION

This invention relates to fractionally crystallizing pure xylitol from an aqueous reaction medium in which the xylitol is formed by reduction of xylose.

In recent years, many attractive processes for making xylitol have been developed. These processes have involved extracting xylose from naturally occurring hemicellulosic plant materials and then reducing the xylose to xylitol.

Hemicellulosic materials such as corncobs, maize, cotton seed hulls and husks, sunflower hulls, oat hulls, peanut shells, rice hulls and husks, and bagasse, particularly oat hulls, have been found to be particularly interesting sources of xylose. Extraction of xylose from such hemicellulosic materials has been conveniently carried out by one or more hydrolysis steps, followed by separation and crystallization of a xylose of high purity. Reduction of the xylose, obtained thereby to xylitol has been suitably carried out in a conventional manner by a chemical or catalytic reduction in an aqueous medium.

However, a significant problem has remained, i.e., how to obtain a substantially pure xylitol from the aqueous medium in which reduction of xylose was carried out. As formed in the aqueous reaction mixture, the xylitol, amounting to about 30 weight percent of the mixture, has been mixed with small amounts of unreduced xylose as well as other residual contaminants from the hemicellulosic material, such as polysaccharides. Typically, the unreacted xylose, usually amounting to about 0.3 to 0.5 weight percent, has been the most serious contaminant. It has been found that adverse physiological effects are associated with ingestion of xylose by mammals, e.g., eye disorders. For this reason, when the xylitol is intended for human consumption, its xylose content must be negligible, i.e., no more than about 0.10 weight percent xylose.

Heretofore, xylitol had been isolated by purifying the aqueous reaction medium with ion exchange resins and then either evaporating off the solvent to leave xylitol as the residue or fractionally crystallizing the xylitol from an alcohol-water mixture. It has been found, however, that isolating xylitol by evaporation yields a product containing substantial amounts of unreduced xylose. On the other hand, when substantially pure xylitol has been isolated by fractional crystallization, an alcohol-water mixture has remained. This alcohol by-product has contained relatively large amounts of xylose and xylitol, as well as of alcohol, which has made it too valuable to be merely thrown away. Moreover, this alchohol by-product has represented a potentially useful source of nutrient material. However, expensive processing has been required in order to recover the alcohol and convert this by-product to a useful, i.e., alcohol-free, nutrient material. There has been an unfilled need therefore for a process for expeditiously obtaining substantially pure xylitol from the aqueous reaction mixture in which it is formed whereby a useful xylose-xylitol by-product is obtained which does not require further involved processing.

SUMMARY OF THE INVENTION

In accordance with this invention, a process is provided for obtaining crystalline xylitol substantially free of xylose from a mixture containing xylitol and xylose which comprises providing an aqueous solution containing 50 to 75% xylitol, less than about 5% xylose and about 20 to 45% water and fractionally crystallizing xylitol from the aqueous solution to provide crystalline xylitol containing no more than about 0.10% xylose.

By the process of this invention, xylitol, containing no more than 0.10% xylose, is obtained in yields of up to 95% from the aqueous reaction medium in which the xylitol was formed from xylose. Also, by this process, a valuable, aqueous by-product containing xylose and xylitol is produced which can be directly used as a nutrient material for cattle.

DETAILED DESCRIPTION OF THE INVENTION

This invention relates to a process for obtaining crystalline xylitol substantially free of xylose from a mixture containing xylitol and xylose by providing an aqueous solution containing about 50 to 75% (weight percent) xylitol, no more than about 5 weight percent xylose and about 20 to 45 weight percent water and then fractionally crystallizing xylitol from the aqueous solution.

The mixture of xylose and xylitol, utilized as the starting material in this invention, can be obtained by reducing xylose to xylitol. This reduction of xylose can be carried out in a conventional manner in an aqueous medium containing 1 to 60 weight percent xylose, preferably 25 to 40 weight percent xylose, with at least 95%, preferably about 99%, of the xylose being reduced to xylitol. In carrying out this reduction of xylose to xylitol to form a xylose and xylitol containing mixture, any conventional method for reducing an aldehyde or keto group in an aqueous medium to an alcohol can be utilized. This reduction can be carried out in a chemical or catalytic way, for example, chemically with sodium amalgam or a complex metal hydride such as lithium borohydride or sodium borohydride. Preferably, a catalytic reduction by hydrogenation with a noble-metal catalyst such as platinum or palladium is utilized. Especially preferred catalysts are nickel catalysts such as Raney-nickel.

The catalytic reduction can be carried out utilizing conventional hydrogenation conditions. In this reaction, temperature, pressure and pH are not critical, and the reaction can be suitably carried out at a temperature of from about 70°C. to 120°C., at hydrogen pressures of from about 10 atm. (gauge) to about 50 atm. (gauge) and at an aqueous pH of 3 to 10. Preferably, the hydrogenation is carried out at a hydrogen pressure of about 30 atm. (gauge) and at a temperature of about 85° to 105°C. The hydrogenation proceeds quantitatively. The solid catalyst system can be easily removed from the aqueous reaction mixture containing the xylitol by conventional processes such as filtration.

The aqueous xylose and xylitol containing mixture, which results from the hydrogenation of xylose, can, if desired, be purified with one or more ion exchange resins. The solution can, for example, be passed through a cationic ion exchange resin bed and then, if desired, through an anionic ion exchange resin bed. Any conventional cationic ion exchange resin, such as a cross-linked polystyrene sulfonic acid cationic ion exchange resin (e.g., polystyrene sulfonic acid type resins), and any conventional anionic ion exchange resin, such as a cross-linked polystyrene containing quaternary ammonium groups or substituted amines, can be utilized in accordance with this invention. By successively passing the hydrogenation reaction medium through a cationic ion exchange resin bed and then through an anionic ion exchange resin bed, all entrained and residual impurities are removed from the xylitol. The effluent from these resins is a colorless, aqueous liquid, containing principally xylose and xylitol.

The aqueous solution containing 50 to 75% xylitol, less than about 5% xylose and 20 to 45% water can be obtained by concentrating the aqueous reaction mixture which results from the reduction of xylose and which may optionally have been treated with one or more ion exchange resins. The concentration of the xylose and xylitol containing reaction mixture can be carried out in a conventional manner. Preferably, the solution is concentrated by heating the solution under reduced pressure at a temperature of about 30° to about 50°C. to evaporate off water.

In accordance with this invention, it has been surprisingly found that fractional crystallization of xylitol from an aqueous solution containing 50 to 75% xylitol and less than about 5% xylose will produce a substantially pure, crystalline xylitol, containing no more than about 0.10% xylose. It has also been found that from an aqueous solution containing 60 to 75% xylose and about 1% or less xylose, crystalline xylitol containing less than 0.05% xylose can be obtained. It has been further found that at a xylitol concentration of about 68%, the yield of crystalline xylitol containing substantially no xylose are maximized.

The fractional crystallization of xylitol in accordance with this invention can be carried out in a conventional manner by cooling the solution from an initial temperature at which it is saturated with xylitol to a lower temperature at which the xylitol will precipitate. In this crystallization, the particular temperature and pressure utilized are not critical, and in general, an initial temperature of room temperature (22°C.) and atmospheric pressure may be suitably utilized. Preferably, fractional crystallization is carried out by slowly cooling the aqueous mixture to below 15°C., with cooling to about 0°C. being particularly preferred.

The xylitol precipitate can be isolated by filtration, washing and drying in a conventional manner. The mother liquor which remains, containing xylitol and xylose, can be conveniently cycled to other crystallization batches.

In accordance with the process of this invention, xylitol of 99% purity, and greater, containing no more than 0.10% xylose, can be obtained, and yields of up to 95% can be achieved with recycling of the mother liquors to subsequent batches. The aqueous mother liquor by-products, after recycling, contain xylose and xylitol and can be incorporated in food for cattle.

The examples which follow further illustrate the invention. All temperatures are in degrees centigrade. Amberlite IR-120 is a cross-linked, polystyrene sulfonic acid cation exchange resin, made by Rohm & Haas, Philadelphia, Pa. Amberlite IRA-93 is a cross-linked, polystyrene quartenary ammonium anion exchange resin, made by Rohm & Haas, Philadelphia, Pa.

EXAMPLE 1

200 grams of dried ground oat hulls having the following compositions:

| | | | |
|---|---|---|---|
| 1. Water | | 7.8 | percent |
| 2. Solids | | 92.2 | percent |
| a. Ash | | 5.4 | percent |
| b. Carbohydrates present in their polysaccharide form. | | | |
| 1) Arabinose | | 2.2 | percent |
| 2) Xylose | | 21.5 | percent |
| 3) Galactose | | 0.7 | percent |
| 4) Glucose | | 2.4 | percent |
| 5) Mannose | | trace | |
| 6) Other hemicelluloses and proteins | | 8–10 | percent | were suspended in 800 ml. of 0.02M aqueous hydrochloric acid. The pH of this suspension was 3.5. This suspension was heated in a sealed pyrex tube at 120°C. for 1 hour. After this period, the reaction mixture was cooled to room temperature, and the solids were filtered off. The filtered solids were then mixed with 800 ml. of 0.175M aqueous hydrochloric acid to produce a pH of 1.1. This mixture was heated in a sealed pyrex tube at 120°C. for one hour. After this period, the reaction mixture was cooled to room temperature and the solids filtered off. The filtered solids were washed with water and the water washes were combined with the filtrate. The filtrate was deionized by passage through a column containing 110 ml. of Amberlite IRA-93 (in its OH⁻form). The column was washed twice, each time with 50 ml. of water (deionized). The combined eluents were concentrated under vacuum to a syrup (10% by weight water content). To this syrup there was added 32 ml. of methanol. The resulting mixture was cooled to −10°C. to produce xylose as its crystalline precipitate. The resulting crystalline precipitate was filtered, and the crystals were washed with 30 ml. of methanol. After washing, the crystals were dried under vacuum to yield 32.5 grams of xylose (96% pure).

EXAMPLE 2

15 grams of xylose (as prepared in Example 1) were dissolved in 22.5 ml. of water. To this solution there was added 3.0 grams of Raney-nickel catalyst (50 percent by weight aqueous suspension) and 0.015 grams of calcium carbonate. This mixture was hydrogenated for about 1.5 hours at a temperature of 100°C. and at a hydrogen pressure of 450 p.s.i.g. After this, the mixture was cooled, and the catalyst was separated therefrom. The catalyst was washed with deionized water. The wash water was combined with the filtrate. The filtrate was passed through a 4 ml. Amberlite IR-120 cation exchange resin (H⁺) and through an 8 ml. Amberlite IRA-93 anionic exchange resin (OH⁻). The columns were washed with water. The eluent and the wash liquor were combined to yield an aqueous solution containing about 30% by weight xylitol and about 0.3 to 0.5% by weight xylose.

EXAMPLE 3

The aqueous hydrogenation solution for each batch made by the procedure of Example 2, containing xylose and xylitol, was concentrated to 70 weight percent total solids by heating at 40°C. The concentrated solution was then slowly cooled over 2 hours to a temperature of 0°C. to 5°C. The xylitol crop which precipitated from each batch was filtered, washed and dried. The mother liquor from each batch was recycled with subsequent, aqueous hydrogenation solution batches until the xylose content of the crop obtained from a particular batch was 0.05 weight percent. Thereafter, the mother liquor was concentrated to 70 weight percent total solids content for each of two subsequent crystallizations, and two further xylitol crops were obtained.

The table which follows summarizes the results for each batch. % is percent by weight. It can be seen from this table that by recycling the mother liquor one can obtain crystalline xylitol containing no more than 0.05% xylose.

Table of Aqueous Xylitol Crystallization Results

| Crystallization Batch | Aqueous Hydrogenation Solution added containing | | Xylitol isolated g | Purity % (glpc) | Xylose Content (%) | Xylitol Yield % | Cumulative Yield % |
|---|---|---|---|---|---|---|---|
| | solids,g | xylitol,g | | | | | |
| 1 | 150.0 | 145.5 | 43.1 | 101.8 | 0 | 29.6 | 29.6 |
| 2 | 150.0 | 145.5 | 108.6 | 100.3 | 0–0.05 | 43.7 | 52.0 |
| 3 | 150.0 | 145.5 | 137.6 | 100.5 | 0–0.05 | 48.3 | 66.2 |
| 4 | 150.0 | 145.5 | 131.5 | 99.6 | 0–0.05 | 44.5 | 72.0 |
| 5 | 150.0 | 145.5 | 147.0 | 100.2 | 0–0.05 | 47.6 | 77.7 |
| 6 | 150.0 | 145.5 | 151.1 | 100.5 | 0–0.05 | 49.2 | 82.2 |
| 7 | 150.0 | 145.5 | 141.5 | 99.9 | 0–0.05 | 47.0 | 84.3 |
| 8 | 0 | 0 | 88.7 | 99.0 | 0.05–0.10 | 54.5 | 92.8 |
| 9 | 0 | 0 | 27.4 | 99.0 | 0.10 | 38.2 | 95.3 |
| TOTAL | 1050.0 | 1018.5 | 977.5 | | | | 95.3 | glpc = gas-liquid phase chromatography

We claim:

1. In a process for obtaining crystalline xylitol substantially free of xylose from a mixture consisting essentially of about 30% xylitol, about 0.3% to about 0.5% xylose and water; said mixture being obtained by hydrogenating an aqueous xylose solution; wherein the improvement comprises:
   a. concentrating said mixture by heating at a temperature of about 30°C. to about 50°C. under reduced pressure to provide an aqueous solution consisting essentially of about 60% to about 75% xylitol, from about 1% to less than about 5% xylose, and water;
   b. fractionally crystallizing xylitol from said aqueous solution by cooling to a temperature below 15°C.;
   c. separating the crystallized xylitol from said solution;
   d. recovering the mother liquor from said crystallization and combining said mother liquor with a subsequent aqueous hydrogenated xylose solution batch; and
   e. recycling the combined solutions of step (d) through steps (a) to (d) to provide crystalline xylitol containing no more than 0.05% xylose.

2. The process of claim 1 wherein said aqueous solution contains about 68% xylitol.

3. The process of claim 1 wherein xylitol is fractionally crystallized by cooling to about 0°C.

* * * * *